United States Patent [19]

Razvan et al.

[11] Patent Number: 5,241,094

[45] Date of Patent: Aug. 31, 1993

[54] BASIC CALCIUM ALUMINUM HYDROXIDE DICARBOXYLATES, A PROCESS FOR THEIR PRODUCTION AND THEIR USE

[75] Inventors: Coriolan Razvan; Reinhard Beck; Alfred Kuerzinger; Albert W. Puerzer; Michael Rosenthal, all of Munich, Fed. Rep. of Germany

[73] Assignee: Baerlocher GmbH, Munich, Fed. Rep. of Germany

[21] Appl. No.: 916,106

[22] PCT Filed: Jan. 7, 1991

[86] PCT No.: PCT/EP91/00077

§ 371 Date: Jul. 21, 1992

§ 102(e) Date: Jul. 21, 1992

[87] PCT Pub. No.: WO91/11421

PCT Pub. Date: Aug. 8, 1991

[30] Foreign Application Priority Data

Feb. 1, 1990 [DE] Fed. Rep. of Germany ....... 4002988

[51] Int. Cl.$^5$ .................. C07F 5/06; C07F 3/04; C08K 5/09; C08K 5/04
[52] U.S. Cl. .................. 556/179; 556/184; 524/399; 524/400
[58] Field of Search ............ 556/179, 184; 524/399, 524/400

[56] References Cited

U.S. PATENT DOCUMENTS

| | | | |
|---|---|---|---|
| 3,398,108 | 8/1968 | Turner | 260/23 |
| 4,008,193 | 2/1977 | Scheidl et al. | 260/23 X |
| 4,590,233 | 5/1986 | Erwied et al. | 524/357 |
| 4,761,188 | 8/1988 | Miyata | 148/6.2 |
| 4,910,246 | 3/1990 | Burba, III et al. | 524/399 |
| 4,963,608 | 10/1990 | Kunieda et al. | 524/394 |
| 5,169,892 | 12/1992 | Kawashima et al. | 524/394 |

FOREIGN PATENT DOCUMENTS

| | | |
|---|---|---|
| 0142773 | 5/1985 | European Pat. Off. . |
| 0189899 | 8/1986 | European Pat. Off. . |
| 0256872 | 2/1988 | European Pat. Off. . |
| 0319086 | 6/1989 | European Pat. Off. . |
| 1219223 | 6/1966 | Fed. Rep. of Germany . |
| 3001093 | 4/1989 | Fed. Rep. of Germany . |
| 2403362 | 4/1979 | France . |
| 52-49258 | 4/1977 | Japan . |
| 0004330 | 1/1980 | Japan .................. 556/179 |
| 1415929 | 12/1975 | United Kingdom . |

Primary Examiner—José G. Dees
Assistant Examiner—Porfirio Nazario
Attorney, Agent, or Firm—Scully, Scott, Murphy & Presser

[57] ABSTRACT

The invention describes basic calcium aluminum hydroxide dicarboxylates of the general formula $$Ca_xAl_2(OH)_{2(x+2)}A \cdot m\, H_2O$$

wherein
x means 2–8,
m means 0–12 and
A means an aliphatic, aromatic or heteroaromatic dicarboxylic acid anion or combinations thereof
and a process for their production.

The compounds according to the invention are especially suited as stabilizers for halogen-containing, thermoplastic resins, in particular PVC.

10 Claims, No Drawings

BASIC CALCIUM ALUMINUM HYDROXIDE DICARBOXYLATES, A PROCESS FOR THEIR PRODUCTION AND THEIR USE

The invention relates to basic calcium aluminum hydroxide dicarboxylates, a process for their production and their use as stabilizers for halogen-containing, thermoplastic resins, in particular polyvinyl chloride.

Thermoplastic, halogen-containing resins, in particular PVC, are instable to the influence of heat and light. A thermal decomposition of the resin already occurs in the processing of e.g. unstablized PVC. This is manifested in a discolouring of the shaped article and in the deterioration of the mechanical properties. To exclude this disadvantage it is necessary to incorporate heat stabilizers into the resin composition. For this purpose, organic and/or inorganic compounds of the metals lead, barium, cadmium, calcium, tin and zinc are customarily added alone or in combinations. In addition to this, other costabilizers such as epoxides, organic sulphur compounds, polyols and phosphites are still added.

Basic lead compounds are preferably used for stabilizing PVC articles such as tubes, plates, profiles and cable insulations. The most frequently used basic lead compounds are of the sulphate, phosphite or stearate type.

De-PS 12 19 223 and DE-OS 24 19 379 teach that PVC cable insulations can preferably be stabilized with 2-basic lead phthalate, since this compound imparts the cable excellent electric properties.

It is mentioned in EP-A- 0 313 113 that 4-basic lead fumarate is the most effective basic lead compound for stabilizing plasticized, halogen-containing vinyl polymer compositions. According to EP-A-O 319 086 5-basic lead fumarate imparts shaped PVC articles a higher stability and a better degree of whiteness than other known lead stabilizers.

The organic and/or inorganic compounds of the heavy metals lead, barium and cadmium are rated as toxic. For this reason, attempts have been made for a long time to replace them by non-toxic compounds. The stabilizers on the basis of combinations of calcium and zinc carboxylates, which are considered to be non-toxic, are insufficient in their effectiveness in most fields of application. Their disadvantages are manifested in a non-sufficient long-term stability and/or an unsatisfactory initial colour and colour retention. The combination of these metallic soaps with effective costabilizers which improve the initial colour and long-term stability is therefore imperative. It is described in FR-A 2 403 362 to stabilize plasticized PVC for cable insulations with a mixture of calcium zinc fatty acids, sorbite and a β-diketone, EP-A- 0256 872 describes the use of hydrotalcite and a β-diketone for stabilizing PVC resins. Alkali alumino silicates in connection with other costabilizers were also suggested to be used in PVC (DE-A- 31 13 442).

However, all non-toxic stabilizing systems suggested so far have disadvantages as compared with heavy metal containing stabilizers. Mostly, they do not have the necessary long-term stability. A good initial colour and a sufficient colour retention can only be achieved by the use of large amounts of expensive "colour improvers". The metal-containing costabilizers hydrotalcite and zeolite are disadvantageous inasmuch as they split off volatile compounds at the processing temperatures necessary for the processing of e.g. PVC, which leads to bubble formation in the shaped article. Shaped PVC articles stabilized e.g. with polyol and/or zeolite take up water, which leads to considerable problems in the further processing.

The invention is based on the object of providing new compounds and a process for their production, which are especially suited as a stabilizer for halogen-containing polymers without having the aforementioned disadvantages of the known stabilizers, and which are in particular regarded as ton-toxic.

This object is accomplished by the invention, on the one hand, by the provision of basic calcium aluminum hydroxide dicarboxylates of the general formula $$Ca_xAl_2(OH)_{2(x+2)}A \cdot m\ H_2O$$

wherein
x means 2–8,
m means 0–12 and
A means an aliphatic, aromatic or heteroaromatic dicarboxylic acid anion or combinations thereof.

X means preferably 3–6 and m means preferably 2–4 in the aforementioned formula.

The dicarboxylic acid anions indicated with A are e.g. derived from malonic acid, succinic acid, adipic acid, fumaric acid, maleic acid, phthalic acid, isophthalic acid, terephthalic acid and pyridine dicarboxylic acids. The fumarate and phthalate anion form part of the preferred dicarboxylic acid anions.

Examinations by means of X-ray diffraction showed that the dicarboxylates according to the invention do not fall under the hydrotalcite type regarding their crystal structure.

It became surprisingly apparent that the calcium aluminum hydroxide dicarboxylates according to the invention impart comparable heat stabilities like basic lead compounds to halogen-containing, thermoplastic resins and shaped articles produced therefrom. The initial colours and the colour retention of e.g. shaped unplasticized PVC articles which are stabilized with one of the new compounds according to the invention are equivalent to the same shaped articles with contain known non-toxic stabilizer systems.

The object on which the invention is based is, on the other hand, solved by a process for the production of the calcium aluminum hydroxide dicarboxylates according to the invention, which is characterized in that mixtures of calcium hydroxide and/or calcium oxide, aluminum hydroxide and sodium hydroxide or of calcium hydroxide and/or calcium oxide and sodium aluminate are reacted with the corresponding dicarboxylic acid in amounts corresponding to the production of the desired compounds in an aqueous medium and the reaction product is separated and recovered in a manner known per se. The reaction product directly obtained from the reaction described above can be separated from the aqueous reaction medium according to known processes, preferably by means of filtration. The processing of the separated reaction product is also carried out in a manner known per se, e.g. by washing the filter cake with water and drying the washed residue at temperatures of e.g. 60°–130° C., preferably at 90°–120° C.

Both a finely divided, active aluminum hydroxide in combination with sodium hydroxide and a sodium aluminate can be used for the reaction. Calcium can be used in the form of finely divided calcium oxide or calcium hydroxide or mixtures thereof.

The reaction temperatures are preferably between about 25° and 100° C., furthermore preferably between about 40° and 85° C. Catalysts or accelerators are not necessary, but can possibly be also used. The crystal water can be removed wholly or partly by thermal treatment in the compounds according to the invention.

If they are used as stabilizers the dried calcium aluminum hydroxide dicarboxylates according to the invention do not split off any water at the processing temperatures of 160°-200° C., which are e.g., customary for unplasticized PVC so that no disturbing bubble formation occurs in the shaped articles.

To improve their dispersibility in halogen-containing, thermoplastic resins the compounds according to the invention can be coated in known fashion with surface-active agents.

According to the invention halogen-containing, thermoplastic resins can be stabilized with the calcium aluminum hydroxide dicarboxylates according to the invention. Polyvinyl chlorides, homopolymers and copolymers thereof and their mixtures with other polymers such as ABS (copolymer of acrylonitrile/butadiene/styrene), CPVC (post-chlorinated PVC), acrylates and the like, which are produced in known fashion, are especially suited for this.

In addition to the compounds according to the invention, further additives can of course be incorporated into the resin. Examples of such additives are: organotin compounds, organic phosphites, epoxy compounds, amino compounds, polyhydric alcohols, metallic soaps of $C_8$-$C_{22}$ fatty acids with the metals Ca, Zn, Mg or Al, antioxidants, UV absorbers, carbonyl compounds, antistatic agents, lubricants, plasticizers, pigments and fillers.

The invention is explained in greater detail by means of the following examples.

A) Production of the basic calcium aluminum hydroxide dicarboxylates according to the invention.

EXAMPLE 1

An aqueous suspension (4.5 l) of 296 g of calcium hydroxide (4 mol) and 164 g of sodium aluminate (2 mol) is heated to 50° C. Subsequently 232 g of fumaric acid (2 mol) is added under stirring in the form of a 10% aqueous solution heated at 85° C. at constant feed rate in the course of 30 minutes. Thereupon the suspension is heated to 70° C. and stirring is carried out at this temperature for 2 hours. 10 minutes before the end of the reaction time 4 g of sodium stearate are added for coating. The suspension obtained in this fashion is filtered off and washed with 1.8 l of water. The filter cake formed in this fashion is dried at 125° C. in a drying cupboard for 4 hours.

The analysis values of the product are indicated below.

|     | Mol ratio |                  |
| --- | --------- | ---------------- |
|     | Found value | Calculated value |
| Ca  | 4.1       | 4.0              |
| Al  | 1.8       | 2.0              |
| C   | 4.3       | 4.0              |

EXAMPLE 2

An aqueous suspension (5.0 l) of 222 g of calcium hydroxide (3 mol), 80 g of sodium hydroxide (2 mol) and 156 g of active aluminum hydroxide (2 mol) is heated to 70° C. Subsequently 332 g of phthalic acid (2 mol) in the form of an 8% aqueous solution (temperature 85° C.) are added under stirring at constant feed rate in the course of 30 minutes. Thereupon the suspension is heated to 80° C. and stirring is carried out at this temperature for 2 hours. 10 minutes before the end of the reaction time 4 g of sodium stearate are added for coating. The suspension obtained in this fashion is filtered off, washed with 1.2 l of water and the filter cake is dried at 130° C. in a drying cupboard for 4 hours. The analysis values of the product produced in this fashion are indicated below.

|     | Mol ratio |                  |
| --- | --------- | ---------------- |
|     | Found value | Calculated value |
| Ca  | 3.05      | 3.0              |
| Al  | 1.95      | 2.0              |
| C   | 7.2       | 8.0              |

B) Use of the compounds according to the invention as stabilizers.

The heat stability and the initial color of shaped PVC bodies to which the compounds according to the invention were been added are evaluated in the following examples.

The mixtures used in the following examples are homogenized and plasticized at 180° C. for 5 minutes on a laboratory rolling mill to evaluate the heat stability. Square sample sheets of an edge length of 15 mm are cut out from the sheet produced in this fashion, which is about 1 mm thick. The sample sheets are tempered in a heating cupboard at 190° C. One sheet each is withdrawn at an interval of 10 minutes and attached to a test card. This process is repeated until the sample sheets have a black discolouring.

EXAMPLE 3

|                          | Parts by weight |      |      |
| ------------------------ | --------------- | ---- | ---- |
|                          | A               | B    | C    |
| PVC (K68)                | 100             | 100  | 100  |
| Impact strength additive | 10              | 10   | 10   |
| Chalk                    | 5               | 5    | 5    |
| TiO$_2$                  | 4               | 4    | 4    |
| Distearyl phthalate      | 0.6             | 0.6  | 0.6  |
| Bisphenol A              | 0.2             | 0.2  | 0.2  |
| Lead stearate            | 1.0             | —    | —    |
| Dibasic lead phthalate   | 2.0             | —    | —    |
| Calcium stearate         | 0.5             | 1.0  | 1.0  |
| Zinc stearate            | —               | 0.5  | 0.5  |
| Ca$_4$Al$_2$(OH)$_{12}$C$_4$H$_2$O$_4$ | — | 3.0 | — |
| Ca$_3$Al$_2$(OH)$_{10}$C$_8$H$_4$O$_4$ | — | —   | 3.0 |
| Dibenzoyl methane        | —               | 0.1  | 0.1  |

The aforementioned compositions of A to C were tested according to the indicated method. The results are summarized in table I.

TABLE I

| Compo- | Results of the evaluation of thermal stability |||||||||||
|        | Time (min.) |||||||||||
| sition | 0 | 10 | 20 | 30 | 40 | 60 | 80 | 100 | 120 | 140 | 160 |
| A      | 1 | 1  | 1  | 3  | 3  | 3  | 3  | 3   | 3   | 3   | 5   |
| B      | 1 | 1  | 1  | 1  | 2  | 2  | 2  | 3   | 4   | 4   | 6   |
| C      | 1 | 1  | 1  | 2  | 2  | 2  | 4  | 4   | 4   | 4   | 6   |

1 = white
2 = slightly yellow
3 = slightly grey
4 = yellow
5 = grey
6 = brown

EXAMPLE 4

| | Parts by weight | | |
|---|---|---|---|
| | D | E | F |
| PVC K70 | 100 | 100 | 100 |
| Chalk | 60 | 60 | 60 |
| TiO$_2$ | 2 | 2 | 2 |
| Dioctyl phthalate | 50 | 50 | 50 |
| Bisphenol A | 0.2 | 0.2 | 0.2 |
| Dibasic lead phthalate | 2.0 | — | — |
| Lead stearate | 1.0 | — | — |
| Calcium stearate | 0.5 | 1.0 | 1.0 |
| Zinc stearate | — | 0.5 | 0.5 |
| Ca$_4$Al$_2$(OH)$_{12}$C$_4$H$_2$O$_4$ | — | 3.0 | — |
| Ca$_3$Al$_2$(OH)$_{10}$C$_8$H$_4$O$_4$ | — | — | 3.0 |

The aforementioned compositions of D to F were tested according to the indicated method and the thermal stability was evaluated. The results are summarized in table II.

TABLE II

| | Time (min.) | | | | | | | | | |
|---|---|---|---|---|---|---|---|---|---|---|
| Composition | 0 | 10 | 20 | 40 | 60 | 80 | 120 | 160 | 180 | 200 |
| D | 1 | 1 | 1 | 1 | 3 | 3 | 3 | 3 | 3 | 5 |
| E | 1 | 1 | 1 | 1 | 2 | 2 | 3 | 3 | 4 | 6 |
| F | 1 | 1 | 1 | 1 | 1 | 2 | 2 | 4 | 4 | 6 |

1 = white
2 = slightly yellow
3 = slightly grey
4 = yellow
5 = grey
6 = brown

What is claimed:

1. A calcium aluminum hydroxide dicarboxylate compound having the general formula $$Ca_xAl_2(OH)_{2(x+2)}A \cdot mH_2O$$

wherein
x is 2 to 8,
m is 0 to 12 and
A is an aliphatic, aromatic or heteroaromatic dicarboxylic acid anion or combinations thereof.

2. A compound according to claim 1 wherein x is 3 to 6.

3. A compound according to claim 1 wherein m is 2 to 4.

4. A compound according to claim 1 wherein A is the fumarate anion.

5. A compound according to claim 1 wherein A is the phthalate anion.

6. A compound according to claim 2 wherein m is 2 to 4.

7. A process for the preparation of the compound of claim 1 comprising
(a) reacting, in an aqueous medium, a mixture of
  (i) calcium hydroxide,
  (ii) calcium oxide or
  (iii) a mixture of (i) and (ii)
with
  (iv) aluminum hydroxide and sodium hydroxide or
  (v) sodium aluminate
with the corresponding dicarboxylic acid in amounts effective to provide said compound of claim 1, and
(b) recovering said compound of claim 1.

8. A process according to claim 7, wherein the reaction is carried out at a temperature between about 25° and 100° C.

9. A process for stabilizing halogen-containing thermoplastic resins comprising combining a stabilizing effective amount of a compound according to claim 1 with a halogen-containing thermoplastic resin.

10. A process according to claim 9 wherein the halogen-containing thermoplastic resin is polyvinyl chloride.

* * * * *